US010869900B2

(12) United States Patent
Funk

(10) Patent No.: US 10,869,900 B2
(45) Date of Patent: Dec. 22, 2020

(54) COMPOSITION AND PRODUCTS COMPRISING SENESCENT CELLS FOR USE IN TISSUE REGENERATION

(71) Applicant: QRSkin GmbH, Würzburg (DE)

(72) Inventor: Martin Funk, Landsberg am Lech (DE)

(73) Assignee: QRSkin GmbH, Würzburg (DE)

( * ) Notice: Subject to any disclaimer, the term of this patent is extended or adjusted under 35 U.S.C. 154(b) by 0 days.

(21) Appl. No.: 15/752,765

(22) PCT Filed: Aug. 11, 2016

(86) PCT No.: PCT/EP2016/069189
§ 371 (c)(1),
(2) Date: Feb. 14, 2018

(87) PCT Pub. No.: WO2017/032614
PCT Pub. Date: Mar. 2, 2017

(65) Prior Publication Data
US 2018/0360889 A1 Dec. 20, 2018

(30) Foreign Application Priority Data
Aug. 21, 2015 (EP) .................................... 15182070

(51) Int. Cl.
*A61K 35/36* (2015.01)
*A61L 15/40* (2006.01)
*A61L 26/00* (2006.01)
*A61K 35/12* (2015.01)
*A61P 17/00* (2006.01)

(52) U.S. Cl.
CPC .............. *A61K 35/36* (2013.01); *A61K 35/12* (2013.01); *A61L 15/40* (2013.01); *A61L 26/0057* (2013.01); *A61P 17/00* (2018.01); *A61L 26/008* (2013.01); *A61L 26/0033* (2013.01); *A61L 26/0047* (2013.01); *A61L 26/0076* (2013.01)

(58) Field of Classification Search
None
See application file for complete search history.

(56) References Cited

U.S. PATENT DOCUMENTS

| | | | |
|---|---|---|---|
| 6,126,935 | A | 10/2000 | Van Bossuyt |
| 6,197,330 | B1 | 3/2001 | Rees et al. |
| 6,673,603 | B2 | 1/2004 | Baetge et al. |
| 7,247,478 | B2 | 7/2007 | Eberhardt et al. |
| 8,323,638 | B2 | 12/2012 | Rolland et al. |
| 2003/0165482 | A1 | 9/2003 | Rolland et al. |
| 2006/0121002 | A1* | 6/2006 | Rolland ................ A61K 35/36 424/93.7 |
| 2006/0177418 | A1 | 8/2006 | Braiman-Wiksman et al. |
| 2007/0258958 | A1 | 11/2007 | Ghosh et al. |
| 2013/0058906 | A1 | 3/2013 | Turzi |
| 2015/0024008 | A1 | 1/2015 | Kron et al. |

FOREIGN PATENT DOCUMENTS

| | | |
|---|---|---|
| CN | 102120031 | 7/2011 |
| CN | 103079577 | 5/2013 |
| WO | 1996014738 | 5/1996 |
| WO | 2002078721 | 10/2002 |

OTHER PUBLICATIONS

Rodier, F., Detection of the senescence-associated secretory phenotype (SASP). In Cell Senescence, 2009, pp. 165-173, Humana Press, Totowa, NJ (English abstract).
Young, A. R. and Narita, M., SASP reflects senescence. EMBO reports, 2009, 10(3), pp. 228-230 (English).
Demaria et al., "An essential role for senescent cells in optimal wound healing through secretion of PDGF-AA." Developmental cell 31 (6), 2014, pp. 722-733 (English).
Zhong et al., Tissue scaffolds for skin wound healing and dermal reconstruction. Wiley Interdisciplinary Reviews: Nanomedicine and Nanobiotechnology, 2(5), 2010, pp. 510-525 (English abstract Wiley Online Library).
International Search Report for PCT Application No. PCT/EP2016/069189 dated Oct. 25, 2016, 9 pages.
Hansbrough et al., Colmposite Grafts of Human Keratinocytes Grown on a Polyglactin Mesh-Cultured Fibroblast Dermal Substitute Function as a Bilayer Skin Replacement in Full-Thickness Wounds on Athymic Mice, J. Burn Care and Rehab, 14(5), 1993, pp. 485-494 (English Abstract), 2 pages.
Kawai et al., Rejection of Cultured Keratinocyte Allografts in Presensitized Mice, Transplantion, 56(2), 1993, pp. 265-269 (English), 5 pages.
Ben-Porath and Weinberg, When Cells Get Stressed: an Integrative View of Cellular Senescence, J. Clin. Invest., 113(1), 2004, pp. 8-13 (English), 7 pages.
Ben-Porath and Weinberg, The Signals and Pathways Activating Cullular Senescence, Int. J. Biochem. Cell Biol., 37(5), 2005, pp. 961-976 (English abstract), 2 pages.
Schmitt, C.A., Senescence, Apoptosis and Therapy—Cutting the Lifelines of Cancer, Nat. Rev. Cancer, 3, 2003, pp. 286-295 (English abstract), 18 pages.
Martin, G.M., Genetic Modulation of Senescent Phenotypes in *Homo sapiens*, Cell, 120 (4), 2005, pp. 523-532 (English), 10 pages.
Balaban et al., Mitochondria, Oxidants, and Aging, Cell, 120(4), 2005, pp. 483-495 (English), 13 pages.
Krtolica et al., Senescent Fibroblasts Promote Ephithelial Cell Growth and Tumorigenesis: A Link Between Cancer and Aging, PNAS, 98(21), pp. 12072-12077 (English), 6 pages.

(Continued)

*Primary Examiner* — Scott Long
*Assistant Examiner* — Evelyn Y Pyla
(74) *Attorney, Agent, or Firm* — Seyfarth Shaw LLP

(57) ABSTRACT

The present invention relates to in vitro cultured senescent cells, such as epithelial cells, keratinocytes and/or fibroblasts as well as their use in the treatment of tissue regeneration, particularly for the treatment of wounds such as burns or ulcers or the treatment of inflammatory conditions. Optionally, products may be used in combination with further drugs including antimicrobial or antidiabetic agents.

15 Claims, 7 Drawing Sheets

(56) References Cited

OTHER PUBLICATIONS

Coppe et al., A Role for Fibroblasts in Mediating the Effects of Tobacco-Induced Epithelial Cell Growth and Invasion, Mol. Cancer Res, 6(7), 2008, pp. 1085-1098 (English), 15 pages.
Coppe et al., The Senescence-Associated Secretory Phenotype: The Dark Side of Tumor Suppression, Annu. Rev. Pathol., 5, 2010, pp. 99-118 (English), 24 pages.
Krizhanovsky et al., Senescence of Activated Stellate Cells Limits Liver Fibrosis, Cell, 134(4), 2008, pp. 657-667 (English), 11 pages.
Sagiv et al., Granule Exocytosis Mediates Immune Surveillance of Senescent Cells, Oncogene, 32, 2013, pp. 1971-1977 (English), 7 pages.
Blagosklonny, M.V., Cell Cycle Arrest is not yet Senescence, which is not just Cell Cycle Arrest: Terminology for TOR-Driven Aging, Aging 4(3), 2012, pp. 159-165 (English), 7 pages.
Blagosklonny, M.V., Cell Cycle Arrest is not yet Senescence, Aging 3(2), 2011, pp. 94-101 (English), 8 pages.
Coppe et al., Senescence-Associated Secretory Phenotypes Reveal Cell-Nonautonomous Functions of Oncogenic RAS and the p53 Tumor Suppressor, PLOS-Biology, 6(12), 2008, pp. 2853-2868 (English), 16 pages.
Pawlikowski et al., Senescence at a Glance, Journal of Cell Science, 126(18), 2013, pp. 4061-4067 (English), 7 pages.
Rheinwald and Green, Serial Cultivation of Strains of Human Epidermal Keratinocytes: the Formation of Keratinizing Colonies from Single Cells, Cell, 6(3), 1975, pp. 331-343 (English abstract), 1 page.
Lewis et al., UVB-induced Senescence in Human Keratinocytes Requires a Functional Insulin-like Growth Factor-1 Receptor and p53, Mol. Biol. Cell, 19(4), 2008, pp. 1346-1353 (English), 8 pages.
Volotskova et al., Targeting the Cancer Cell Cycle by Cold Atmospheric Plasma, Scientific Reports, 2, 636, 2012, pp. 1-10 (English), 10 pages.
Mosesson MW. Fibrinogen and fibrin structure and functions. J Thromb Haemost. 2005:3(8):1894-904.
Martino MM, Briquez PS, Ranga A, Lutolf MP, Hubbell JA. Heparin-binding domain of fibrin(ogen) binds growth factors and promotes tissue repair when incorporated within a synthetic matrix. Proceedings of the National Academy of Sciences of the United States of America. 2013;110(12):4563-8.
Sahni A. Oddjin T. Francis CW. Binding of basic fibroblast growth factor to fibrinogen and fibrin. The Journal of biological chemistry. 1998;273(13):7554-9.
Sahni A, Sporn LA, Francis CW. Potentiation of endothelial cell proliferation by fibrin(ogen)-bound fibroblast growth factor-2. The Journal of biological chemistry. 1999;274(21):14936-41.
Becker JC, Domschke W, Pohle T. Biological in vitro effects of fibrin glue: fibroblast proliferation, expression and binding of growth factors. Scand J Gastroenterol. 2004;39(10):927-32.
Sahni A, Guo M, Sahni SK, Francis CW. Interleukin-1beta but not IL-1alpha binds to fibrinogen and fibrin and has enhanced activity in the bound form. Blood. 2004;104(2):409-14.
Geer DJ, Swartz OD, Andreadis ST. Biomimetic delivery of keratinocyte growth factor upon cellular demand for accelerated wound healing in vitro and in vivo. The American journal of pathology. 2005;167(6):1575-86.
Muhamed I, Sproul EP. Ligler FS, Brown AC. Fibrin Nanoparticles Coupled with Keratinocyte Growth Factor Enhance the Dermal Wound-Healing Rate. ACS applied materials & interfaces. 2019;11(4):3771-80.
Kim I, Lee SK, Yoon JI. Kim DE, Kim M, Ha H. Fibrin glue improves the therapeutic effect of MSCs by sustaining survival and paracrine function. Tissue engineering Part A. 2013;19(21¬22):2373-81.
Van de Kamp J, Jahnen-Dechent W, Rath B. Knuechel R, Neuss S. Hepatocyte growth factor-loaded biomaterials for mesenchymal stem cell recruitment. Stem cells international. 2013;2013:892065, 9 pages.
Hopfner U, Aitzetmueller MM, Nessbach P, Hu MS, Machens HG, Maan ZN, et al. Fibrin Glue Enhances Adipose-Derived Stromal Cell Cytokine Secretion and Survival Conferring Accelerated Diabetic Wound Healing. Stem cells International. 2018;2018:1353085, 9 pages.
Law JX, Chowdhury SR. Aminuddin BS, Ruszymah BHI. Role of plasma-derived fibrin on keratinocyte and fibroblast wound healing. Cell and tissue banking. 2017;18(4):585-95.
Cook PW, Pittelkow MR, Shipley GD, Latkowski JM, Freedberg IM, Blumenberg M, et al. Growth factor-independent proliferation of normal human neonatal keratinocytes: production of autocrine- and paracrine-acting mitogenic factor. Journal of cellular physiology. 1991:146(2):277-89.
Gille J, Khalik M, Konig V, Kaufmann R. Hepatocyte growth factor/scatter factor (HGF/SF) induces vascular permeability factor (VPFNEGF) expression by cultured keratinocytes. The Journal of investigative dermatology. 1998:111(6):1160-5.
Latkowski JM. Freedberg IM, Blumenberg M. Keratinocyte growth factor and keratin gene regulation. J Dermatol Sci. 1995;9(1):36-44.
Werner S, Krieg T, Smola H. Keratinocyte-fibroblast interactions in wound healing. The Journal of investigative dermatology. 2007;127(5):998-1008.
Wojta J, Kaun C. Breuss JM, Koshelnick Y, Beckmann R, Hattey E, et al. Hepatocyte growth factor increases expression of vascular endothelial growth factor and plasminogen activator inhibitor-1 in human keratinocytes and the vascular endothelial growth factor receptor flk-1 in human endothelial cells. Laboratory investigation; a journal of technical methods and pathology. 1999;79(4):427-38.
Giri H, Cai X, Panicker SR, Biswas I, Rezaie AR. Thrombomodulin Regulation of Mitogen-Activated Protein Kinases. International journal of molecular sciences. 2019;20(8).
Chan CP, Chang MC, Wang YJ, Chen LI, Tsai YL, Lee JJ, et al. Thrombin activates Ras-CREB/ATF-1 signaling and stimulates c-fos, c-jun, and c-myc expression in human gingival fibroblasts. J Periodontol. 2008;79(7):1248-54.
Dawes KE, Gray AJ, Laurent GJ. Thrombin stimulates fibroblast chemotaxis and replication. Eur J Cell Biol. 1993;61(1):126-30.
Sower LE. Froelich CJ. Carney DH. Fenton JW, 2nd, Klimpel GR. Thrombin induces IL-6 production in fibroblasts and epithelial cells. Evidence for the involvement of the seven-transmembrane domain (STD) receptor for alpha-thrombin. Journal of immunology (Baltimore. Md : 1950). 1995;155(2):895-901.
Wang L, Luo J, Fu Y, He S. Induction of interleukin-8 secretion and activation of ERK1/2, p38 MAPK signaling pathways by thrombin in dermal fibroblasts. Int J Biochem Cell Biol. 2006;38(9):1571-83.
Algermissen B, Sitzmann J, Nurnberg W, Laubscher JC. Henz BM, Bauer F. Distribution and potential biologic function of the thrombin receptor PAR-1 on human keratinocytes. Archives of dermatological research. 2000;292(10):488-95.
Gugerell A, Schossleitner K, Wolbank S, Numberger S, Red H, Guile H, et al. High thrombin concentrations in fibrin sealants induce apoptosis in human keratinocytes. Journal of biomedical materials research Part A. 2012;100(5):1239-47.
Talati N, Kamato 0, Piva TJ, Little PJ, Osman N. Thrombin promotes PAI-1 expression and migration in keratinocytes via ERK dependent Smad linker region phosphorylation. Cell Signal. 2018;47:37-43.
Bassus S, Herkert 0. Kronemann N, Gorlach A, Bremerich D., Kirchmaier CM, et al. Thrombin causes vascular endothelial growth factor expression in vascular smooth muscle cells: role of reactive oxygen species. Arteriosder Thromb Vasc Biol. 2001;21(9):1550-5.
Cao H, Dronadula N. Rao GN. Thrombin induces expression of FGF-2 via activation of PI3K-Akt-Fra-1 signaling axis leading to DNA synthesis and motility in vascular smooth muscle cells. Am J Physiol Cell Physiol. 2006;290(1):C172-82.
Cucina A. Borrelli V. Lucarelli M, Sterpetti AV, Cavallaro A. Strom R. et al. Autocrine production of basic fibroblast growth factor translated from novel synthesized mRNA mediates thrombin-induced mitogenesis in smooth muscle cells. Cell Biochem Fund. 2002;20(1):39-46.
Derian CK, Eckardt A.J. Andrade-Gordon P. Differential regulation of human keratinocyte growth and differentiation by a novel family of protease-activated receptors. Cell Growth Differ. 1997;8(7):743-9.

(56) References Cited

OTHER PUBLICATIONS

Shimaya Y, Shimada M. Shutto Y, Fujita T, Murakami R. Nakamura N. et al. Thrombin stimulates synthesis of macrophage colony-stimulating factor, granulocyte-macrophage colony-stimulating factor and granulocyte colony-stimulating factor by human proximal tubular epithelial cells in culture. Nephron Extra. 2012;2(1):1-8.

Wakita H, Furukawa F, Takigawa M. Thrombin and trypsin induce granulocyte-macrophage colony-stimulating factor and interleukin-6 gene expression in cultured normal human keratinocytes. Proc Assoc Am Physicians. 1997;109(2)190-207.

Hoffman M, Cooper ST. Thrombin enhances monocyte secretion of tumor necrosis factor and interleukin-1 beta by two distinct mechanisms. Blood Cells Mol Dis. 1995;21(2)156-67.

Goedkoop R, Juliet R, You PH, Daroczy J, de Roos XP, Lijnen R. et al. Wound stimulation by growth-arrested human keratinocytes and fibroblasts: HP802-247, a new-generation allogeneic tissue engineering product. Dermatology. 2010;220(2)114-20.

Gough, Science Signaling, Jan. 2015, 8(358), pp. ec3 (English).

Serrano, Dev Cell, "Senescence Helps Regeneration," Dec. 22, 2014, 31, pp. 671-672 (English).

Demaria et al., Dev Cell. "An Essential Role for Senescent Cells in Optimal Wound Healing through Secretion of PDGF-AA," Dec. 22, 2014; 31(6), pp. 722-733 (English).

Tsai et al, Cancer Res 2005, 65 (15), pp. 6734-6744, 11 pages.

Papadopoulou and Kletsas, International Journal of Oncology, 39 (2011), pp. 989-999, 11 pages.

Alessio et al, Oncotarget, 6 (10), 2015, pp. 8155-8166, 12 pages.

Dierick et al, FEBS Letters 531 (3), 2002, pp. 499-504, 6 pages.

Pascal et al, FEBS Letters 579 (17), 2005, pp. 3651-3659, 9 pages.

Ewald et al, J Biomol Screen 14 (7), 2009, pp. 853-858, 6 pages.

* cited by examiner

FIG. 1

| SASP factors | | secreted * | intracellular+ |
|---|---|---|---|
| **Chemokines** | | | |
| | *IL8* | 2105 +/- *488* | 29 |
| | *GRO alpha* | 3977 +/- *705* | 57 |
| **Growth factors** | | | |
| | *VEGF* | 8543 +/-*684* | 48 |
| | *endothelin* | 192 +/- *5* | 26 |
| **Proteases and regulators** | | | |
| | *MMP 7* | 48677 +/- *26915* | 1809 |
| | *MMP 9* | 6383 +/- *2900* | 3507 |
| | *MMP 10* | 75850 +/- *35553* | 14637 |
| | *MMP 12* | 22713 +/- *5210* | 52 |
| | *MMP 13* | 4554 +/- *1291* | 426 |
| | *TIMP 1* | 140960 +/- *79799* | 1036 |
| | *TIMP 2* | 25362 +/- *15086* | 2521 |
| **TGF beta 1** | | 5532 +/- *543* | n.d. |

* pg/ml supernatant

+ pg/mg protein extract

ß-galactisodase staining of keratinocyte cell layer

Anti LAMP-1 staining of keratinocyte cell layer

Anti-phospho-histone H2A.X staining of keratinocyte cell layer

FIG. 5
Time to healing of burn wounds
| | | | | | | | | | | | | | | | | | | | | | |
|---|---|---|---|---|---|---|---|---|---|---|---|---|---|---|---|---|---|---|---|---|---|
| Age (y) | 1 | 3 | 4 | 5 | 6 | 7 | 8 | 9 | 10 | 11 | 12 | 13 | 14 | 15 | 16 | 17 | 18 | 21 | 26 | 35 | 36 |
| No. Patients | 1 | 9 | 32 | 73 | 38 | 38 | 24 | 18 | 17 | 13 | 7 | 3 | 8 | 5 | 2 | 3 | 1 | 2 | 1 | 1 | 1 |
| % of total | 0,3% | 3,0% | 10,8% | 24,6% | 12,8% | 12,8% | 8,1% | 6,1% | 5,7% | 4,4% | 2,4% | 1,0% | 2,7% | 1,7% | 0,7% | 1,0% | 0,3% | 0,7% | 0,3% | 0,3% | 0,3% |
| % acumulated | | 3% | 14% | 39% | 52% | 64% | 72% | 78% | 84% | 89% | 91% | 92% | 95% | 96% | 97% | 98% | 98% | 99% | 99% | 99% | 100% |
Fig. 6
SASP profile depending on growth stimulus
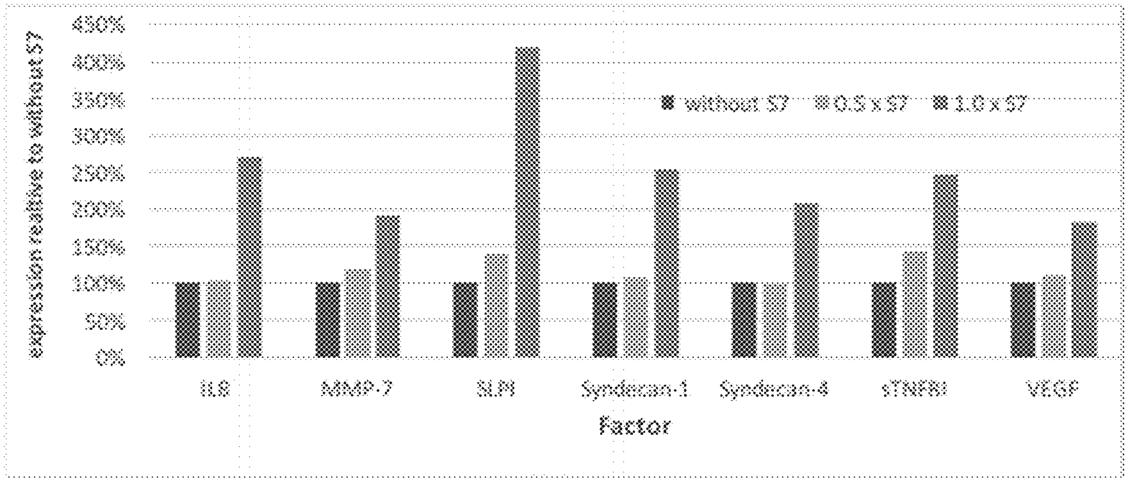
FIG. 7
SASP profile of cells in replicative senescence
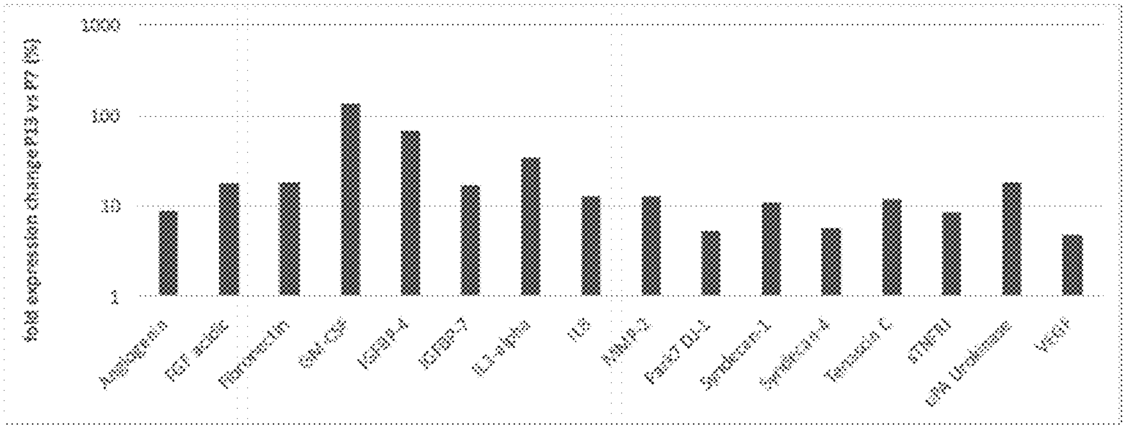

SASP profile of senescent cells treated with t-BHP or Ethanol

SASP profile of senescent cells treated with surfactant

ß-galactosidase staining of irradiated fibroblasts

FIG. 11

SASP profile of cells treated with Mitomycin C

| Treatment | Cell type | Mitomycin (uM) | ß-Gal posotive cells | Fold secretion compared to control (0 uM mitomycin) | | | | | | | | | |
|---|---|---|---|---|---|---|---|---|---|---|---|---|---|
| | | | | Angiogenin | FGF acidic | IGFBP-4 | IL1-alpha | IL6 | IL8 | MMP-2 | SLPI | Syndecan-4 | TIMP-1 |
| Single | SCRC 1041 | 0 | 6,6% | 1 | 1 | 1 | 1 | 1 | 1 | 1 | 1 | 1 | 1 |
| | | 0,05 | 18,2% | 1,5 | 1,1 | 1,1 | 1,0 | 1,0 | 0,7 | 1,2 | 1,0 | 1,1 | 1,0 |
| | | 0,2 | 17,9% | 0,8 | 1,0 | 0,8 | 0,9 | 1,1 | 1,3 | 0,9 | 0,9 | 0,8 | 1,0 |
| | | 2 | 4,8% | 0,9 | 1,1 | 0,8 | 1,2 | 1,8 | 2,5 | 1,1 | 0,9 | 1,0 | 1,3 |
| | BKB1002 | 0 | 1,5% | 1 | 1 | 1 | 1 | 1 | 1 | 1 | 1 | 1 | 1 |
| | | 0,05 | 2,0% | 1,8 | 2,0 | 1,8 | 2,4 | 2,6 | 2,0 | 2,0 | 2,2 | 1,8 | 1,9 |
| | | 0,2 | 2,2% | 0,6 | 0,8 | 0,5 | 0,6 | 0,8 | 0,5 | 0,8 | 0,7 | 0,8 | 0,7 |
| | | 2 | 3,4% | 1,4 | 2,1 | 1,5 | 2,2 | 3,9 | 1,8 | 2,1 | 2,5 | 2,6 | 1,9 |
| Repeated | BKB1002 | 0 | 10,2% | 1 | 1 | 1 | 1 | 1 | 1 | 1 | 1 | 1 | 1 |
| | | 0,2 | 10,2% | 317,1 | 2,9 | 24,2 | 4,3 | 2,1 | 2,0 | 2,2 | 1,7 | 101,1 | 2,4 |
| | | 0,5 | 14,4% | 360,9 | 3,9 | 24,0 | 7,9 | 5,1 | 5,6 | 3,7 | 6,5 | 268,4 | 2,8 |
| | | 1 | 27,1% | 387,9 | 7,1 | 33,6 | 18,6 | 7,8 | 8,9 | 3,4 | 5,0 | 485,6 | 3,8 |
| | | 2 | 37,7% | 396,2 | 6,8 | 34,6 | 15,9 | 8,2 | 13,7 | 3,6 | 6,3 | 254,9 | 3,0 |

COMPOSITION AND PRODUCTS COMPRISING SENESCENT CELLS FOR USE IN TISSUE REGENERATION

FIELD OF THE INVENTION

The invention relates to in vitro cultured senescent cells, such as epithelial cells, keratinocytes and/or fibroblasts as well as their use in the manufacture of products for tissue regeneration, particularly for the treatment of wounds such as burns or ulcers.

BACKGROUND OF THE INVENTION

Biologically active products comprising cells, for example allogeneic keratinocytes, either alone or in combination, are well established the manufacture of products for treating wounds, particularly burns or ulcers. While in former times allogeneic keratinocytes were mainly used for skin replacement (see for example Hansbrough J F, Morgan J L, Greenleaf G E and Bartel R., 1993. *J. Burn Care and Rehab.* 14 (5), 485-494), it was found that the success of the treatment is not due to the keratinocytes growing into the wound and "replacing" cells. Instead, transplanted keratinocytes solely remain at the wound for a certain period of time and then vanish or are removed, but stimulate the body's own healing process by re-epithelialization due to a complex network of secreted factors (see for example Kawai K, Ikarashi Y, Tomiyama K, Matsumoto Y, Fujiwara M, Transplantation, 1993 August; 56(2):265-9).

Notably, keratinocytes' products known in the art mainly focus on proliferating cells.

For example, U.S. Pat. No. 7,247,478 B2 relates to keratinocytes with a high proliferation potential as well as to products comprising said keratinocytes and a carrier.

Further, US 20070258958 A1 describes interactive wound covers comprising actively proliferating keratinocytes on a biopolymer membrane.

U.S. Pat. No. 6,126,935 A relates to pellets obtained from keratinocytes remaining the ability to proliferate and their use in wound healing.

Moreover, WO02078721 A (EP 1450827 B1) describes the use of a two-constituent compositions for the in situ production of cell transplants comprising both, fibroblasts and keratinocytes cultured in suspension.

U.S. Pat. No. 6,673,603 B2 shows a cell paste for tissue regeneration, e.g., in the treatment of skin wounds containing a combination of fibroblasts and keratinocytes that secrete biologically active substances, admixed with an extracellular matrix material such that the admixture forms a viscous cell paste. These may be rendered mitotically inactivated by irradiation or Mitomycin C.

Moreover, U.S. Pat. No. 8,323,638 B2 describes a cell preparation consisting of fibroblasts and keratinocytes, which might be applied to a wound side either in form of a spray or a paste.

However, the keratinocyte products known in the art are either complex to gain, cumbersome to applicate, intricate to store and/or do not provide an optimal cocktail of biologically active factors particularly suitable for efficiently treating wounds. Hence, there is a need and thus it is an object of the present invention to provide an effective composition for improving tissue regeneration, particularly for improving the treatment of wounds and inflammatory conditions. Furthermore, it is an object to provide an improved biologically active product that is easy to handle in terms of application and/or storage.

These as well as further objects, which will become apparent from the following description of the present invention, are attained by the subject matter of the independent claims. Some of the preferred embodiments of the present invention are defined by the subject matter of the dependent claims.

SUMMARY OF THE INVENTION

Various aspects, advantageous features and preferred embodiments of the present invention as summarized in the following items, respectively alone or in combination, contribute to solving the object of the invention.

1. Composition comprising a cell component, wherein the cell component includes a senescent cell type or a combination of senescent cell types, and wherein the composition is for use in tissue regeneration.
2. Composition according to item 1, wherein the senescent cell type derives from cells selected from the group consisting of epithelial cells, corneal epithelial cells, keratinocytes, fibroblasts, melanocytes, endothelial cells, pericytes, monocytes, lymphocytes, thrombocytes, mast cells, adipocytes, muscle cells, neurons, osteocytes, osteoblasts, chondrocytes, mesenchymal stem cells and/or an adult or embryonic stem cells, preferably wherein the senescent cell type derives from cells selected from the group consisting of epithelial cells, corneal epithelial cells, keratinocytes, fibroblasts, melanocytes, endothelial cells, pericytes, monocytes, lymphocytes, thrombocytes, mast cells, adipocytes, mesenchymal stem cells and/or an adult or embryonic stem cells.
3. Composition according to item 1 or 2, wherein the cell component includes more than 10%, preferably more than 30% senescent cells, further preferably more than 50% senescent cells, still more preferably more than 70% senescent cells, and particularly more than 90% senescent cells, either selected from one senescent cell type or a combination of senescent cell types as defined above.
4. Composition according to any of the preceding items, wherein the cells are allogeneic, autogeneic, transgenic or xenogeneic, preferably allogeneic.
5. Composition according to any of the preceding items, wherein the cell component includes mainly one cell type, the cell type being keratinocytes, preferably wherein at least 50% of all cells are keratinocytes, preferably at least 75% of all cells are keratinocytes, more preferably at least 85% of all cells in the composition are keratinocytes.
6. Composition according to item 5, wherein from said keratinocytes more than 10% are senescent, preferably more than 30% are senescent, further preferably more than 50% are senescent, more preferably more than 70% are senescent, in particular more than 90% are senescent.
7. Composition according to any of the preceding items, wherein the cell component includes mainly senescent keratinocytes, preferably more than 10% senescent keratinocytes, further preferably more than 30% senescent keratinocytes, more preferably more than 50% senescent keratinocytes, even more preferably more than 70% senescent keratinocytes, particularly more than 90% senescent keratinocytes.

8. Composition according to any of the preceding items, wherein the keratinocytes are prepared from a human skin or foreskin, preferably from a human neonatal foreskin.
9. Composition according to any of the preceding items, wherein the cells are undifferentiated or differentiated.
10. Composition according to any of the preceding items, wherein senescence is induced in vitro.
11. Composition according to any of the preceding items, wherein senescence is replicative, stress induced or premature senescence, preferably stress induced or premature senescence.
12. Composition according to any of the preceding items, wherein senescence is induced either by cell culture stress, oxidative stress/reactive oxygen species, senescence-inducing administration of mitomycin C or any other chemically-based mitotic inhibitor, administration of surfactants or other small molecule inducers of senescence, irradiation with γ-Rays, irradiation with X-Rays, or irradiation with UV light, such as UVB, or treatment with cold plasma, radiation or e-beam treatment.
13. Composition according to any of the preceding items, wherein senescence is induced by cell culture stress selected from the group consisting of cell overgrowth, cell contact inhibition, and high cell density, preferably by cell contact inhibition.
14. Composition according to any of the preceding items, wherein senescence is characterized by cell cycle arrest in the presence of growth stimulation, preferably wherein senescence is induced by cell cycle arrest in the presence of sustained growth stimulation, more preferably wherein senescence is induced by cell contact inhibition in the presence of sustained growth stimulation.
15. Composition according to any of the preceding items, wherein senescent cells express and/or secrete one or more biologically active molecules selected from the group consisting of: IL-1α, IL-1β, IL-6, IL-7, IL-8, IL-10, IL-13, IL-15, IL-18, MCP1, MCP2, MCP4, MIF, MIP-1a, MIP-3a, HCC-4, Eotaxin-3, TECK, ENA-78, I-309, I-TAC, GROα, GROβ, GROγ, VEGF, EGF, HGF, FGF, bFGF, KGF, Amphiregulin, Angiogenin, APOJ, CAV1, OSTEO, Epiregulin, Heregulin, SCF, SDF-1alpha, PlGF, IGFBP-2, -3, -4, -6, -7, GM-CSF, PDGF-BB, TGF-α, TGF-β1, TGF-β2, TGF-β3, ICAM1, ICAM3, TRAIL-R3, Fas, OPG, SGP130, EGF-R uPAR, sTNFRI, sTNFRIII, MMP1, MMP2, MMP3, MMP7, MMP9, MMP10, MMP12, MMP13, MMP14, TIMP1, TIMP2, PAI1, PAI2, Park7 DJ-1, uPA/Urokinase, SLPI, Syndecan 1, -4, Tenascin C, Endothelin, Collagens, Fibronectins, Laminins, preferably selected from the group consisting of: IL-8, GROα, VEGF, endothelin, MMP7, MMP9, MMP10, MMP12, MMP13, TIMP1, TIMP2, TGF-11, even more preferably comprises at least IL-8, GROα, VEGF, endothelin, MMP7, MMP9, MMP10, MMP12, MMP13, TIMP1, TIMP2 and TGF-β1.
16. Composition according to any of the preceding items, wherein senescent cells are characterized by one or more of features selected from the group consisting of: Senescence Associated (SA) β-gal activity, proliferation arrest, $p16^{INK4a}$ expression, DNA-damage signalling, telomere dysfunction, loss of lamin B1, more preferably shows at least SA β-gal activity and/or proliferation arrest.
17. Composition according to any of the preceding items, wherein senescent cells express and/or secrete at least IL-8, GROα, VEGF, endothelin, MMP7, MMP9, MMP10, MMP12, MMP13, TIMP1, TIMP2 and TGF-11 and show SA β-gal activity and proliferation arrest.
18. Composition according to any of the preceding items, wherein senescence is characterized by one or more of the following morphological features: Enlarged, flattened morphology, hypertrophy, enlarged nuclei, chromatin remodeling reorganization of chromatin through formation of senescence-associated heterochromatic foci (SAHF), prominent Golgi apparatus and vacuolated cytoplasm.
19. Composition according to any of the preceding items for use in the treatment of wounds.
20. Composition according to item 17, wherein the wounds are acute or chronic wounds.
21. Composition according to item 17 or 18, wherein the wounds are wounds of the skin, preferably wherein the wounds were treated by debridement before treatment with the composition and/or wherein the wounds were generated by split skin grafting and/or plastic surgery.
22. Composition according to any of items 17 to 19, wherein the wounds are burns.
23. Composition according to any of items 17 to 20, wherein the wounds are superficial and/or deep partial thickness burns.
24. Composition according to any of items 17 to 21, wherein the wounds are second or third degree burns, preferably second degree burns.
25. Composition according to any of items 17 to 22, wherein the wounds are sun burns.
26. Composition according to any of items 17 to 19, wherein the wounds are chronic wound-healing disorders selected from the group consisting of ulcers, pressure sores, diabetic foot syndrome.
27. Composition according to item 24, wherein the ulcer is selected from the group consisting of ischemic, arterial, venous, neurotrophic, vasculitis, hypertensive and Pyoderma Gangrenosum, decubitus ulcers.
28. Composition according to any of the preceding items in combination with compression or negative pressure therapy.
29. Composition according to any of items 17 to 19, wherein the wound is selected from the group consisting of abrasions, any trauma, radiotherapy lesions, all types of skin loss.
30. Composition according to any of the preceding items for the treatment of an inflammatory condition of skin and subcutaneous tissue, wherein the inflammatory condition is preferably selected from the group consisting of: Erythematosquamous dermatosis, Atopic dermatitis and related conditions, Contact dermatitis and other eczema, Dermatitis due to substances taken internally, Bullous dermatoses, Erythematous conditions, Psoriasis and similar disorders, Lichen, Pruritus and related conditions, and other diseases of skin and subcutaneous tissue like Actinic keratosis, Alopecia and Acne.
31. Composition according to any of the preceding items, further comprising a carrier.
32. Composition according to item 29, wherein the carrier is a wound dressing, a paste, a spray or an ointment, preferably a wound dressing.
33. Composition according to item 29 or 30, wherein the carrier is jelly gauze, preferably petroleum jelly gauze and/or wherein the carrier is comprised of or contains allgenates, collagen, polyuratane foames, hydrocolloids, hydrofibers, hydrogels, hyaluronic acid, cellulose, an acellular animal or human derived product from skin or intestine like Oasis or biosynthetic materials like Laserskin or Suprathel.

34. Composition comprising a combination of a cell component and a substance selected from the group of: antimicrobial agents, antidiabetic agents, mRNA or miRNA antagonists against mRNAs or miRNAs over expressed in chronic, non-healing wounds, growth factors like for example PDGF, FGF-2, VEGF-A, -B, -C, -D, GM-CSF, SDF-1alpha, IL1-beta or peptides derived from these growth factors, inhibitors of enzymes being involved in cortisol synthesis, particularly CYP11B1 overexpressed in chronic wounds as well as of Prolyl-4-hydroxylase, elastase, GSK3β phosphorylation and Cx43, and wherein the cell component includes a senescent cell type or a combination of senescent cell types, preferably wherein the composition is for use in tissue regeneration, more preferably for use according to any of the preceding items.

35. Composition according to item 32, wherein the antimicrobial agent is an antibiotic and/or an antifungal agent, preferably wherein the antibiotic is selected from the group consisting of: cephalosporines, particularly Cefazolin, Cefoxitin, Cefofetan; macrolides, particularly erythromycin; sulphonamides particularly Mafenide; penicillins, chlorhexidine, silver sulfadiazine, silver nitrate and silver derived formulations, and/or wherein the antidiabetic agent is a DDP-4 inhibitor.

36. Composition comprising a senescent cell lysate, wherein the senescent cell lysate derives from senescent cells as defined in any of items 1 to 17 and wherein the composition is for use as defined in any of items 1 to 28.

37. Composition according to item 34, further comprising a carrier as defined in any of items 29 to 31.

38. Composition according to item 34 or 35, further comprising an antimicrobial agent, preferably an antibiotic and/or an antifungal agent, preferably wherein the antibiotic is selected from the group consisting of: cephalosporines, particularly Cefazolin, Cefoxitin, Cefofetan; macrolides, particularly erythromycin; sulphonamides particularly Mafenide; penicillins, chlorhexidine, silver sulfadiazine, silver nitrate and silver derived formulations and/or an antidiabetic agent, preferably a DDP-4 inhibitor and/or mRNA or miRNA antagonists against mRNAs or miRNAs over expressed in chronic, non-healing wounds, growth factors like for example PDGF, FGF-2, VEGF-A, -B, -C, -D, GM-CSF, SDF-1alpha, IL1-beta or peptides derived from these growth factors, inhibitors of enzymes being involved in cortisol synthesis, particularly CYP11B1 overexpressed in chronic wounds as well as of Prolyl-4-hydroxylase, elastase, GSK3β phosphorylation and Cx43.

39. Composition according to any of the items 34 to 36 in combination with compression or negative pressure therapy.

40. Composition comprising senescent cell supernatant, wherein the supernatant has been obtained from senescent cells as defined in any of items 1 to 17 and wherein the composition is for use as defined in any of items 1 to 28.

41. Composition according to item 38, further comprising a carrier as defined in any of items 29 to 31.

42. Composition according to item 38 or 39, further comprising an antimicrobial agent, preferably an antibiotic and/or an antifungal agent, preferably wherein the antibiotic is selected from the group consisting of: cephalosporines, particularly Cefazolin, Cefoxitin, Cefofetan; macrolides, particularly erythromycin; sulphonamides particularly Mafenide; penicillins, chlorhexidine, silver sulfadiazine, silver nitrate and silver derived formulations and/or an antidiabetic agent, preferably a DDP-4 inhibitor and/or mRNA or miRNA antagonists against mRNAs or miRNAs over expressed in chronic, non-healing wounds, growth factors like for example PDGF, FGF-2, VEGF-A, -B, -C, -D, GM-CSF, SDF-1alpha, IL1-beta or peptides derived from these growth factors, inhibitors of enzymes being involved in cortisol synthesis, particularly CYP11B1 overexpressed in chronic wounds as well as of Prolyl-4-hydroxylase, elastase, GSK3β phosphorylation and Cx43.

43. Composition according to any of the preceding items 38 to 40 in combination with compression or negative pressure therapy.

44. Product comprising a carrier and a component selected from the group consisting of senescent cells, senescent cell lysates and senescent cell supernatants, wherein the senescent cells, senescent cell lysates and/or senescent cell supernatants are as defined in any of the preceding items, and wherein the product is for use as defined in any of the preceding items.

45. Product according to item 42, wherein the carrier is a wound dressing.

46. Product according to item 42 or 43, wherein the carrier is jelly gauze, preferably petroleum jelly gauze.

47. Product according to any of items 42 to 44, wherein the carrier is comprised of or contains allgenates, collagen, polyuratane foames, hydrocolloids, hydrofibers, hydrogels, hyaluronic acid, cellulose, an acellular animal or human derived product from skin or intestine like Oasis or biosynthetic materials like Laserskin or Suprathel.

48. Product according to any of items 41 to 45, further comprising an antimicrobial agent, preferably an antibiotic and/or an antifungal agent, preferably wherein the antibiotic is selected from the group consisting of: cephalosporines, particularly Cefazolin, Cefoxitin, Cefofetan; macrolides, particularly erythromycin; sulphonamides particularly Mafenide; penicillins, chlorhexidine, silver sulfadiazine, silver nitrate and silver derived formulations and/or an antidiabetic agent, preferably a DDP-4 inhibitor and/or mRNA or miRNA antagonists against mRNAs or miRNAs over expressed in chronic, non-healing wounds, growth factors like for example PDGF, FGF-2, VEGF-A, -B, -C, -D, GM-CSF, SDF-1alpha, IL1-beta or peptides derived from these growth factors, inhibitors of enzymes being involved in cortisol synthesis, particularly CYP11B1 overexpressed in chronic wounds as well as of Prolyl-4-hydroxylase, elastase, GSK3β phosphorylation and Cx43.

49. Product according to any of items 41 to 46 in combination with compression or negative pressure therapy.

50. Wound dressing colonized with cells as defined in any of items 1 to 16 for the treatment of wounds or inflammatory conditions as defined in any of items 17 to 28.

51. Wound dressing according to item 48, wherein the wound dressing is jelly gauze, preferably petroleum jelly gauze and/or the senescent cells are keratinocytes.
52. Use of a composition or a product according to any of the preceding items 1 to 49 for preparing a medicament for treating wounds and/or inflammatory conditions.
53. Use according item 50, wherein the wounds or inflammatory conditions are as defined in any of items 17 to 28.
54. Process for preserving a composition comprising senescent cells, senescent cell lysates and/or senescent cell supernatants as defined in any of items 1 to 41 or a product according to any of items 42 to 49, wherein the composition or product is cryopreserved, preserved by drying or freeze drying or preserved by treatment with cold plasma, radiation or e-beam treatment.
55. Composition, product or use according to any of the preceding items, wherein the senescent cells were cultured in vitro before combining with the carrier or grown on the carrier or in combination with the carrier.
56. Composition comprising SASP factors selected from a group consisting of IL-1α, IL-1β, IL-6, IL-7, IL-8, IL-10, IL-13, IL-15, IL-18, MCP1, MCP2, MCP4, MIF, MIP-1a, MIP-3a, HCC-4, Eotaxin-3, TECK, ENA-78, I-309, I-TAC, GROα, GROβ, GROγ, VEGF, EGF, HGF, FGF, bFGF, KGF, Amphiregulin, Angiogenin, APOJ, CAV1, OSTEO, Epiregulin, Heregulin, SCF, SDF-1 alpha, PIGF, IGFBP-2, -3, -4, -6, -7, GM-CSF, PDGF-BB, TGF-α, TGF-β1, TGF-β2, TGF-β3, ICAM1, ICAM3, TRAIL-R3, Fas, OPG, SGP130, EGF-R uPAR, sTNFRI, sTNFRIII, MMP1, MMP2, MMP3, MMP7, MMP9, MMP10, MMP12, MMP13, MMP14, TIMP1, TIMP2, PAI1, PAI2, Park7 DJ-1, uPA/Urokinase, SLPI, Syndecan 1, -4, Tenascin C, Endothelin, Collagens, Fibronectins, Laminins, preferably selected from the group consisting of: IL-8, GROα, VEGF, endothelin, MMP7, MMP9, MMP10, MMP12, MMP13, TIMP1, TIMP2, TGF-β1, even more preferably comprises at least IL-8, GROα, VEGF, endothelin, MMP7, MMP9, MMP10, MMP12, MMP13, TIMP1, TIMP2 and TGF-β1.
57. Composition according to item 54, wherein the SASP factors are obtained from senescent cells as defined in any of the preceding items.
58. Composition according to item 54 or 55 in combination with an agent and/or a therapy as defined in any of the preceding items.

BRIEF DESCRIPTION OF THE DRAWINGS

FIG. 1 is a table showing the results of SASP factor protein expression and secretion in epidermal neo-natal foreskin keratinocytes, which senescent cells can be used in an embodiment of the present invention.

FIG. 5 shows the results of clinical studies using keratinocyte cell layers in an embodiment of the present invention.

FIG. 6 shows a SASP profile of human primary keratinocytes (BKB12002) depending on growth stimulus.

FIG. 7 shows a SASP profile of cells in replicative senescence of primary human keratinocytes (BKB12002).

FIG. 11 shows a SASP profile of cells treated with Mitomycin C.

DETAILED DESCRIPTION OF THE INVENTION

Figure 2:
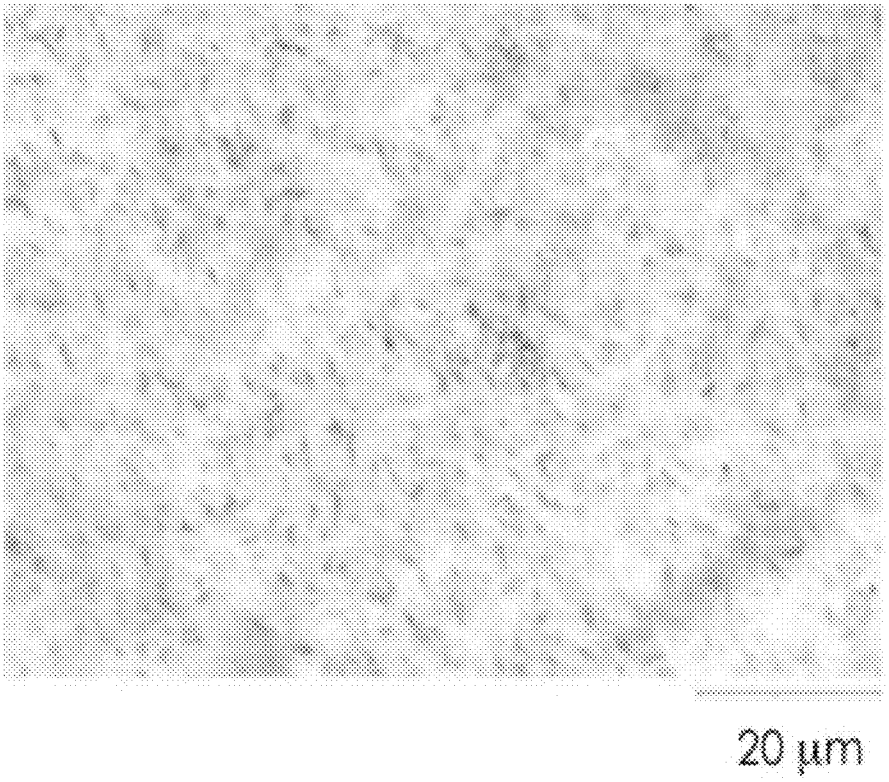
FIG. 2 shows a β-galactisodase staining of a keratinocyte cell layer, which is typical, yet exemplary of senescent cells that can be used in an embodiment of the present invention.

The present invention is now described in more detail by preferred embodiments and examples, which are however presented for illustrative purposes only and shall not be understood as limiting the scoop of the present invention in any way.

The present invention comprises a composition including senescent cells as defined above for improving tissue regeneration, particularly for wound healing. Thus, it is particularly suitable and useful for the treatment of wounds, including any acute and/or chronic wound, for example wounds of the skin such as burns, preferably superficial and deep partial thickness burns and/or second degree burns, or chronic wound-healing disorders selected from the group consisting of ulcers, particularly ischemic, arterial, venous, neurotrophic, vasculitis, hypertensive and Pyoderma Gangrenosum, decubitus ulcers or pressure sores, diabetic foot syndrome or wherein the wound is an abrasions, trauma, radiotherapy lesion or any type of skin lose or an inflammatory conditions of the skin and subcutaneous tissue like Erythematosquamous dermatosis, Atopic dermatitis and related conditions, Contact dermatitis and other eczema, Dermatitis due to substances taken internally, Bullous dermatoses, Erythematous conditions, Psoriasis and similar disorders, Lichen, Pruritus and related conditions, and other diseases of skin and subcutaneous tissue like Actinic keratosis, Alopecia and Acne.

"(Cellular) senescence" is a mechanism that occurs in vivo and in vitro locking the cell into a cell cycle arrest, and in this conventional context was known to inhibit malignant transformation and to contribute to aging. A wide range of different stress factors are reported to trigger cellular senescence (Ben-Porath I, Weinberg R A, *J.Clin.Investig.* 2004; 113:8-13; Ben-Porath I, Weinberg R A, *Int. J. Biochem. Cell Biol.* 2005; 37:961-76). These include telomeric dysfunction upon repeated cell division (replicative senescence), oxidative stress, mitochondrial deterioration, severe or irreparable DNA damage and chromatin disruption (genotoxic stress) and the expression of certain oncogenes (Schmitt C A. *Nat. Rev. Cancer.* 2003; 3:286-95; Martin G M, *Cell.* 2005; 120:523-32; Balaban R S, Nemoto S, Finkel T, *Cell.* 2005; 120:483-95). Besides its well-established role as being a potent tumor suppressive mechanism and a contributor to aging, there is evidence for senescent cells developing altered secretory activities thus promoting tumorigenesis (Krtolica A, Parrinello S, Lockett S, Desprez P, Campisi J; *Proc. Natl. Acad. Sci. USA.* 2001; 98:12072-77; Coppé J P, Boysen M, Sun C H, Wong B J, Kang M K, et al., *Mol. Cancer Res.* 2008; 6:1085-98). For example, Coppé and colleagues described, that fibroblasts having a senescent-associated secretory phenotype thus turning senescent fibroblasts into proinflammatory cells that have the ability to promote tumour progression (Coppé J P, Desprez P Y, Krtolica A, Campisi J. *Annu Rev Pathol.* 2010; 5:99-118). Recently, a fourth role of senescence has been emerged, when Krizhanovsky et al. discovered that tissue damage-induced hyperproliferation of hepatic stellate cells (HSCs) induces cell senescence leading to a reduction in the secretion of extracellular matrix (ECM) proteins and enhanced secretion of ECM degrading proteins, thereby limiting fibrosis upon tissue damage within the liver (Krizhanovsky V, Yon M, Dickins R A, Heam S, Simon J, Miething C, Yee H, Zender L, Lowe S W (2008), *Cell* 134(4):657-667; 54. Sagiv A, Biran A, Yon M, Simon J, Lowe S W, Krizhanovsky V, (2013) *Oncogene* 32(15):1971-1977). Preferably, "senescence" shall not be simply reduced to cell cycle arrest. Rather, senescence can be caused by growth stimulation, when the cell cycle is arrested (Blagosklonny M V, March 2012, AGING Vol 4, No 3, pp 159-165; AGING, February 2011, Vol 3, No 2, pp 94-101). Thus, as one further hallmark, senescent cells may lose the potential to resume proliferation.

However, a senescent cell is a potentially persisting cell that is metabolically active and has undergone extensive changes in the protein expression and secretion pattern, thus finally developing its individual SASP resembling a kind of finger print (Coppé J P, Desprez P Y, Krtolica A, Campisi *J. Annu Rev Pathol.* 2010; 5:99-118). This fact may explain the four obviously opposing functions of senescent cells mentioned above highlighting the importance of the cellular context, i.e. cell type and senescence-inducing stimulus (Coppé J P, Desprez P Y, Krtolica A, Campisi *J. Annu Rev Pathol.* 2010; 5:99-118; Coppé J P, Patil C K, Rodier F, Sun Y, Munoz D P, et al. *PLoS Biol.* 2008; 6:2853-68). The SASP (senescence-associated secretory phenotype), also termed senescence-messaging secretome resembling another hallmark of senescence may include the expression/secretion of the following biologically active factors (Pawlikowski J S, Adams P D and Nelson D M, Sep. 15, 2013 *J Cell Sci* 126, 4061-4067):

i. Interleukins, such as IL-1α, IL-1β, IL-6, IL-7, IL-13, IL-15;
ii. Chemokines, such as IL-8, MCP2, MCP4, GROα, GROβ, GROγ;
iii. Growth factors, such as EGF, HGF, VEGF;
iv. Receptors and ligands, such as ICAM1, ICAM3, TRAIL-R3, Fas, uPAR, sTNFRI, sTNFRIII;
v. Proteases and regulators, such as MMP1, MMP3, MMP10, MMP12, TIMP1, TIMP2, PAI1, PAI2,
vi. Extracellular insoluble molecules, such as Collagens, Fibronectins, Laminins.

In addition to the above mentioned cell cycle arrest and the specific SASP, a senescent cell may be characterized by the following hallmarks (Pawlikowski J S, Adams P D and Nelson D M, Sep. 15, 2013 *J Cell Sci* 126, 4061-4067):

a. Enlarged, flattened morphology
b. $p16^{INK4a}$ expression
c. elevated lysosomal activity (senescence-associated b-galactosidase; SA b-gal)
d. DNA-damage response
e. chromatin remodelling
f. autophagy.

Surprisingly and distinct from prior investigations of related products, it was found by the present inventor that particularly senescent cells show a complex SASP providing a cocktail of biologically active factors that is specifically effective in stimulating the body's own re-epithelization. The correlation between the intended therapeutic effect and associated cellular status of senescence has been experimentally demonstrated, as described in the Examples and as illustrated in the drawings. Thus, the general inventive concept is to make beneficial use of senescence in wound and inflammation therapy. Contrary, biologically active products known in the art as mentioned above mainly focus on cells characterized by a high proliferation rate, thus suppressing senescence pathways.

"Senescent cells" as understood in the present invention are cells characterized by cell cycle arrest, further typically characterized by a SASP comprising one or more of the following factors: IL-1α, IL-1β, IL-6, IL-7, IL-8, IL-1β, IL-13, IL-15, IL-18, MCP1, MCP2, MCP4, MIF, MIP-1a, MIP-3a, HCC-4, Eotaxin-3, TECK, ENA-78, I-309, I-TAC, GROα, GROβ, GROγ, VEGF, EGF, HGF, FGF, bFGF, KGF, Amphiregulin, Epiregulin, Heregulin, SCF, SDF-1 alpha, PIGF, IGFBP-2, -3, -4, -6, -7, GM-CSF, PDGF-BB, TGF-α, TGF-β1, TGF-β2, TGF-33, ICAM1, ICAM3, TRAIL-R3, Fas, OPG, SGP130, EGF-R uPAR, sTNFRI, sTNFRIII, MMP1, MMP3, MMP7, MMP9, MMP10, MMP12, MMP13, MMP14, TIMP1, TIMP2, PAI1, PAI2, SLPI, Endothelin, Collagens, Fibronectins, Laminins, preferably one or more of the following: IL-8, GROα, VEGF, endothelin, MMP7, MMP9, MMP10, MMP12, MMP13, TIMP1, TIMP2, TGF-β1, even more preferably comprises at least IL-8, GROα, VEGF, endothelin, MMP7, MMP9, MMP10, MMP12, MMP13, TIMP1, TIMP2 and TGF-β1.

Furthermore, "senescent cells" as understood in the present invention are cells characterized by cell cycle arrest, further typically characterized by a SASP comprising one or more of the following factors: IL-1α, IL-113, IL-6, IL-7, IL-8, IL-1β, IL-13, IL-15, IL-18, MCP1, MCP2, MCP4, MIF, MIP-1a, MIP-3a, HCC-4, Eotaxin-3, TECK, ENA-78, I-309, I-TAC, GROα, GROβ, GROγ, VEGF, EGF, HGF, FGF, such as FGF acidic, bFGF, KGF, Amphiregulin, Angiogenin, APOJ, CAV1, OSTEO, Epiregulin, Heregulin, SCF, SDF-1 alpha, PIGF, IGFBP-2, -3, -4, -6, -7, GM-CSF, PDGF-BB, TGF-α, TGF-β1, TGF-β2, TGF-33, ICAM1, ICAM3, TRAIL-R3, Fas, OPG, SGP130, EGF-R uPAR, sTNFRI, sTNFRIII, MMP1, MMP2, MMP3, MMP7, MMP9, MMP10, MMP12, MMP13, MMP14, TIMP1, TIMP2, PAI1, PAI2, Park7 DJ-1, uPA/Urokinase, SLPI, Syndecan 1, -4, Tenascin C, Endothelin, Collagens, Fibronectins, Laminins, preferably one or more of the following: IL-8, GROα, VEGF, endothelin, MMP7, MMP9, MMP10, MMP12, MMP13, TIMP1, TIMP2, TGF-β1, even more preferably comprises at least IL-8, GROα, VEGF, endothelin, MMP7, MMP9, MMP10, MMP12, MMP13, TIMP1, TIMP2 and TGF-β1.

The expression and/or secretion of said SASP factors may be increased in senescence-induced cells compared to the corresponding control cells, i.e. non-senescent cells. Preferably, the expression and/or secretion of said SASP factors is significantly increased. Significance may be calculated by any mathematical method known in the art, for example by Student's t-test. As meant herein, the expression and/or secretion of the above-mentioned SASP factors is increased, if it is at least 1.5 fold higher compared to the corresponding control cells. Preferably, the expression is at least 2 fold, further preferably at least 3 fold, even further preferably at least 5 fold, more preferably at least 10 fold, even more preferably at least 20 fold, in particular at least 50 fold higher compared to the control cells.

Moreover, senescent cells of the present invention may particularly show SA β-gal activity, proliferation arrest, $p16^{INK4a}$ expression, DNA-damage signalling, telomere dysfunction, and/or loss of lamin B1, at least proliferation arrest and/or SA β-gal activity. Furthermore, they may show an increased LAMP 1 or phospho-histone H2A.X expression.

Additionally, senescent cells of the present invention may show the following morphological features: Enlarged, flattened morphology, hypertrophy, enlarged nuclei, chromatin remodeling reorganization of chromatin through formation of senescence-associated heterochromatic foci (SAHF), prominent Golgi apparatus and vacuolated cytoplasm. Moreover, senescence according to the invention may be replicative, i.e. dependent on telomere shortening or premature senescence, i.e. in the absence of any detectable telomere loss or dysfunction.

Notably, it has been found that the composition according to the invention is particularly effective when comprising more than 30% in-vitro cultured senescent cells in the cell component, preferably more than 50% in-vitro cultured senescent cells, more preferably more than 70% in-vitro cultured senescent cells, and even more preferably more than 90% in-vitro cultured senescent cells. Alternatively, more than 10% in-vitro cultured senescent cells in the cell component, preferably more than 30% in-vitro cultured senescent cells, more preferably more than 50% in-vitro cultured senescent cells, even more preferably more than 70% in-vitro cultured senescent cells and in particular more than 90% in-vitro cultured senescent cells, are particularly effective.

The cells according to the invention either include one senescent cell type or a combination of senescent cells types. For example, cells from which the senescent cells used according to the invention derive, may be selected from the group consisting of epithelial cells, corneal epithelial cells, keratinocytes, fibroblasts, melanocytes, endothelial cells, pericytes, monocytes, lymphocytes, thrombocytes, mast cells, adipocytes, muscle cells, neurons, osteocytes, osteoblasts, chondrocytes, mesenchymal stem cells and/or an adult or embryonic stem cells. Preferably, the cells from which the senescent cells used according to the invention derive, may be selected from the group consisting of epithelial cells, corneal epithelial cells, keratinocytes, fibroblasts, melanocytes, endothelial cells, pericytes, monocytes, lymphocytes, thrombocytes, mast cells, adipocytes, mesenchymal stem cells and/or an adult or embryonic stem cells. Furthermore, the cells according to the invention may be genetically engineered to secrete SASP factors as defined above. This secretion may be constitutive or may be controlled by gene switching. Additionally, the cells according to the invention may include non-senescent cells.

All cells according to the invention may be autologous, allogeneic, or xenogeneic, preferably allogeneic. Preferably, the cells according to the invention are human. Furthermore, the cells may be transgenic.

Particularly, the cells according to the invention include keratinocytes, more particularly primary epidermal keratinocytes, for example keratinocytes isolated from a donor. These keratinocytes may be isolated from a human adult or neonatal skin, preferably from a human neonatal foreskin. The isolation and initial cultivation of keratinocytes may be carried out by anyone skilled in the art, for example according to the process described by Rheinwald and Green in 1975 (Cell, Volume 6, Issue 3, November 1975, Pages 331-343). However, these keratinocytes may also include keratinocyte cell lines.

In a preferred embodiment, keratinocytes resemble the main cell type of the composition of the present invention, i.e. at least 50% of all cells in the composition are keratinocytes, preferably at least 75-85% of all cells in the composition are keratinocytes, more preferable at least 85-95% of all cells in the composition are keratinocytes. They may be senescent and/or non-senescent. Out of these, preferably more than 10% are senescent, further preferably more than 30%, even more preferably more than 50%, still more preferably more than 70%, in particular more than 90%.

In a preferred embodiment of the present invention, cells are cultured in vitro. Then, senescence according to the invention is induced either by inappropriate growth conditions leading to cell culture stress, for example overgrowth of the cells, high cell density, cell contact inhibition, presence of $H_2 0_2$, presence of ROS, administration of mitomycin C or any other chemically-based mitotic inhibitor, irradiation with γ-Rays, irradiation with X-Rays, or irradiation with UV light, particularly UVB as for example described by Lewis et al. (Mol Biol Cell. 2008 Apr.; 19(4): 1346-1353), and treatment with cold plasma (Volotskova et al., Sci Rep. 2012; 2:636, doi: 10.1038/srep00636.).

In another embodiment of the present invention, senescence according to the invention is induced by oxidative stress/reactive oxygen species, radiation or e-beam treatment.

Furthermore, senescence according to the invention is induced by sublethal doses of surfactants, for example NP-40, preferably in a concentration of 1-10 μM, Triton X-100, preferably in a concentration of 2-20 μM, SDS, Tween 20, Tween 80, preferably in a concentration of 5-20 μM, cardiolipin, and soap. For inducing senescence, cells are cultured with surfactants in sublethal concentrations, for example for one to six weeks.

Alternatively, senescence may be induced by low-dose ionizing radiation as for example described by Tsai K. C. et al. (Cancer Res 2005; 65(15): 6734-44), Papadopoulou A. and Kletsas D. (INTERNATIONAL JOURNAL OF ONCOLOGY 39: 989-999, 2011, DOI: 10.3892/ijo.2011.1132), and Alessio N. et al. (Oncotarget, Vol. 6, No. 10, 2015, pp. 8155-8166).

Alternatively, relatively low levels of Mitomycin C have been found to be senescence-inducing, for example in a concentration of 0.02-1 μM. Preferably, the cell culture medium including Mitomycin C in the above-mentioned concentrations is changed for several times, for example for 2 to 7 time, for example every day to every third day. Then, also slightly lower doses of Mitomycin C may induce senescence.

Alternatively, t-BHP or Ethanol and small molecule inducers of senescence in suitable concentrations, as for example described elsewhere (Dierick, J. F. et al. (2002), FEBS Lett 531(3): 499-504; Pascal, T. et al (2005), FEBS Lett 579(17): 3651-3659; Ewald, J. A. et al. (2009), J Biomol Screen 14(7): 853-858 may be used for inducing senescence.

The respectively used method is controlled, for example by using appropriate concentration and treatment duration of the respective agent or appropriate intensity and duration of the respective physical treatment, to the extent that the senescent cell cycle arrest is attained, which can be verified by any one of the above described characteristics of senescence or SASP.

In a preferred embodiment, senescence according to the invention may be induced, e.g. by any one of the above methods or treatments in the presence of a sustained growth stimulus, i.e. the growth stimulus is applied concurrently to cell cycle arrest. In other words: senescence according to this invention may be induced by coupling cell cycle arrest, preferably by contact inhibition with a growth stimulus. Such growth stimulus according to the invention, may be selected from the means consisting of: media components like serum or serum components in particular from xenogenic or human source, platelets, platelet lysates or components of the later as well as single or combination of growth factors like for example EGF, KGF, FGF, insulin, hydrocortisone or apotransferrin in concentrations known by a person skilled in the art. A further growth stimulus may be TGF-β.

Moreover, cell cycle arrest/proliferation may be analyzed by methods known in the art, for example DNA stains involving 3H-thymidine or BrdU or staining of cell cycle regulators.

In a further aspect, the invention relates to a product for use as mentioned above comprising the senescent cells, preferably senescent epithelial cells, keratinocytes and/or fibroblasts and particularly senescent keratinocytes as mentioned above, and a suitable carrier or carrier material. A suitable carrier or carrier material according to the present invention may be any biocompatible matrix or membrane, for example in form of a wound dressing or gauze including for example films, such as polyurethane films, hydrocarbons, such as petroleum jelly, hydrocolloids, hydrogels, hydrophilic or hydrophobic foams, and calcium alginates, and any solvents, dispersion media, coatings, isotonic solutions and the like, respectively compatible with biologics administration, for example water, saline, finger's solutions, dextrose solution, and 5% human serum albumin, liposomes and non-aqueous vehicles such as fixed oils known in the art, as well as additives such as absorption delaying agents. The carrier or carrier material may be partially or totally colonized with the aforementioned cells. In a preferred embodiment of the present invention, the carrier is a wound dressing, preferably a jelly gauze, more preferably petroleum jelly gauze.

Depending on the carrier or carrier material mentioned above, the composition of the present invention is in form of a (wound) dressing, a paste, a spray, or an ointment. Moreover, a product according to the invention is administered or applied topically, subcutaneously or via inhalation.

In another aspect, the invention relates to a product comprising senescent cell lysates including whole cell lysates or lysates from a particular cell compartment, or comprise senescent cell supernatants, respectively obtained from the above mentioned cells and optionally a carrier as defined above. The lysate or supernatant may or may not still contain cellular material, no matter of still being viable or not. Further, a product for use according to the invention may comprise a cocktail of biologically active factors—including the factors in their isolated form—characteristic for the SASP of senescent cells as described elsewhere herein, and optionally a carrier as described above. In this embodiment the "senescent cell component" according to the present invention means cell lysate or senescent cell supernatant, or SASP factor isolate respectively obtained from senescent cells disclosed herein, optionally in combination with a suitable carrier, respectively.

The aforementioned lysate, supernatant or SASP isolate can respectively be combined with a further therapeutic substance (additional component) as further described below.

The preferred list of SASP factors present in the composition used according to the present invention as well as their concentrations useful for the specified therapy are listed in Table 1 below:

TABLE 1

| | Secreted (pg/ml) | | | Intracellular (pg/mg protein extract) | | |
|---|---|---|---|---|---|---|
| | at least | Suitable and optional upper limit | preferred | at least | Suitable and optional upper limit | preferred |
| IL8 | 50 | 5000 | 200-3000 | 5 | 500 | 20-100 |
| GRO alpha | 100 | 5000 | 250-5000 | 5 | 500 | 20-100 |
| VEGF | 500 | 20000 | 2000-12000 | 5 | 500 | 20-100 |
| Endothelin | 10 | 1000 | 20-300 | 5 | 500 | 20-100 |
| MMP7 | 1000 | 150000 | 8000-80000 | 100 | 10000 | 1000-10000 |
| MMP9 | 500 | 20000 | 2400-10000 | 100 | 10000 | 1000-10000 |
| MMP10 | 10000 | 82000 | 30000-82000 | 1000 | 20000 | 5000-20000 |
| MMP12 | 50 | 50000 | 400-36000 | 5 | 100 | 20-100 |
| MMP13 | 10 | 10000 | 90-7500 | 50 | 1000 | 200-1000 |
| TIMP1 | 20000 | 400000 | 55000-350000 | 100 | 10000 | 1000-10000 |
| TIMP2 | 1000 | 100000 | 5000-60000 | 100 | 10000 | 1000-10000 |
| TGf beta 1 | 500 | 15000 | 1000-7000 | 5 | 1000 | 20-1000 |

Furthermore, the above specified products may additionally include viable and/or dead cells.

Depending on the nature of the wound or inflammatory condition, the invention further relates to a pharmaceutical combination comprising a product according to the invention together with an antimicrobial agent, for example an antibiotic or an antifungial agent including antibiotics from the class of cephalosporines, for example Cefazolin, Cefoxitin, Cefofetan; macrolides, for example erythromycin; sulphonamides, for example Mafenide; penicillins, chlorhexidine, silver sulfadiazine, silver nitrate and silver derived formulations or—in the context of a diabetic wound—in combination with an antidiabetic drug, for example a DDP-4 inhibitor, such as Linagliptin, Sitagliptin, Vildagliptin or Saxagliptin. Moreover, the pharmaceutical combination may include additionally or instead of the above-mentioned agents antagonists against mRNAs or miRNAs over expressed in chronic, non-healing wounds; growth factors like for example PDGF, FGF-2, VEGF-A, -B, -C, -D, GM-CSF, SDF-1alpha, IL1-beta or peptides derived from these growth factors; inhibitors of enzymes being involved in cortisol synthesis, particularly CYP11B1 overexpressed in chronic wounds as well as of Prolyl-4-hydroxylase, elastase, GSK3β phosphorylation and Cx43.

The additional component (e.g. antimicrobial agent, antidiabetic drug or other agent as mentioned above) may be administered or applied prior to, concurrently or consecutively, preferably concurrently with the product mentioned above. Hence, one preferred embodiment relates to a kit comprising a product as defined above and any agent as mentioned above, preferably an antimicrobial agent and/or an antidiabetic agent, preferably a DDP-4 inhibitor.

Moreover, the composition as mentioned above may be used in combination with compression or negative pressure therapy.

In a further aspect, the invention relates to the use of senescent cells or a product or combination as mentioned above for preparing a medicament for treating wounds and/or inflammatory conditions.

In another aspect, the invention relates to a process of cryopreserving senescent cells or a product as mentioned above by freezing, drying or freeze drying.

The compositions mentioned above may be included in a container, pack, or dispenser together with instructions for administration. The dosage regimen is selected from an ordinarily skilled physician or veterinarian according to a variety of factors including species, age, weight, sex, and medical condition of the patient, the type and severity of wound, the form of administration, and the particular cell type.

The following Examples illustrate preferred embodiments of the present invention. Wound dressing assembly and cryopreservation can be carried out as described in WO96/14738A (EP0790767B), notably as described in Example 1 thereof.

Example 1

Preparation and Culture of Human Allogenic Keratinocytes, Senescence Induction:

The keratinocytes according to the invention are isolated according to the process described by Rheinwald and Green in 1975 (Cell, Volume 6, Issue 3, November 1975, Pages 331-343) from skin biopsies from foreskin or other sites, preferably from human neonatal foreskin. In the final production run of the cell layer keratinocytes cells were seeded at a density of 5000 cells/$cm^2$ and cultivated for 14 days without splitting of cells and applying 4 medium changes.

The medium was supplemented with combination of growth factors including FCS (4%), EGF (10 ng/μl), insulin (0.12 U/μl), hydrocortisone (0.8 μg/μl), or apotransferrin (5 μg/μl) in order to keep a constant high growth stimulus. After 6-9 days cells slowed down or stopped proliferation and finally at the end of cultivation displayed a senescence phenotype as also shown in FIG. 2.

Determination of Senescence by Analyzing the SASP

In order to determine the type and the amount of SASP factors secreted by senescence-induced keratinocytes, supernatants from the cell culture flasks after the final cultivation step prior to cryopreservation of the cells were collected and protein concentrations of SASP factors were measured as shown in FIG. 1. Protein concentrations were quantified using the Bio-Plex® Multiplex Immunoassays or ELISA kits from BIO-RAD. FIG. 1 (secreted) shows the concentrations of secreted factors as mean values and corresponding standard deviations from supernatants of three cell culture flasks.

Intracellular levels of SASP factors of cryopreserved epidermal sheets were quantified in protein extracts obtained by lysis of a cell layer using the Bio-Plex™ Cell Lysis Kit from BIO-RAD. Concentrations of SAP factors determined as described above given in pg factor/μg protein extract are depicted in FIG. 1 (intracellular).

Senescence according to the invention may additionally or alternatively be analyzed by SA β-Gal stain or by immune stain using anti-LAMP 1 and/or H2A.X antibodies as illustrated in Example 2 below.

Example 2

2.1 Determination of Senescence by SA β-Gal Staining

Preparation and culture of human allogenic keratinocytes and senescence induction are carried out as described above.

As marker for cellular senescence, β-Gal staining from cryopreserved epidermal sheets was performed using the Senescence β-Galactosidase Staining Kit from Cell Signaling. 1 $cm^2$ of the epidermal sheet was incubated in 2 ml β-Galactosidase Staining Solution at 37° C. overnight, rinsed 5 times with 2 ml PBS and analyzed by light microscopy as shown in FIG. 2.

2.2 Determination of Senescence by Immune Staining Against LAMP 1 and H2A.X

Preparation and culture of human allogenic keratinocytes and senescence induction were carried out as described above. As marker for cellular senescence, immune staining of cryopreserved epidermal sheets was performed using rabbit anti-phospho-histone H2A.X or rabbit anti-LAMP 1 from Cell Signaling. The assay was performed according to the protocol provided by the supplier. To enhance or to enable the immunoreaction between the antibody and the antigen a heat-induced hydrolysis (microwave) as antigen retrieval was performed. The immunoreaction was detected via an anti-rabbit or anti-mouse secondary antibody conjugated with a peroxidase polymer. 3,3'-Diaminobenzidine (DAB) was used as a chromogen. For a more differentiated analysis of the processed sections the slides were counterstained with haematoxylin, which generates an adequate contrast by darkening the DAB signal and providing a blue to violet staining to cell nuclei and a light blue staining to somatic components and fibers. To detect unspecific bindings of the secondary antibody the primary antibody was omitted and replaced by a pre-incubation solution (containing only PBS and BSA).

Figure 3:
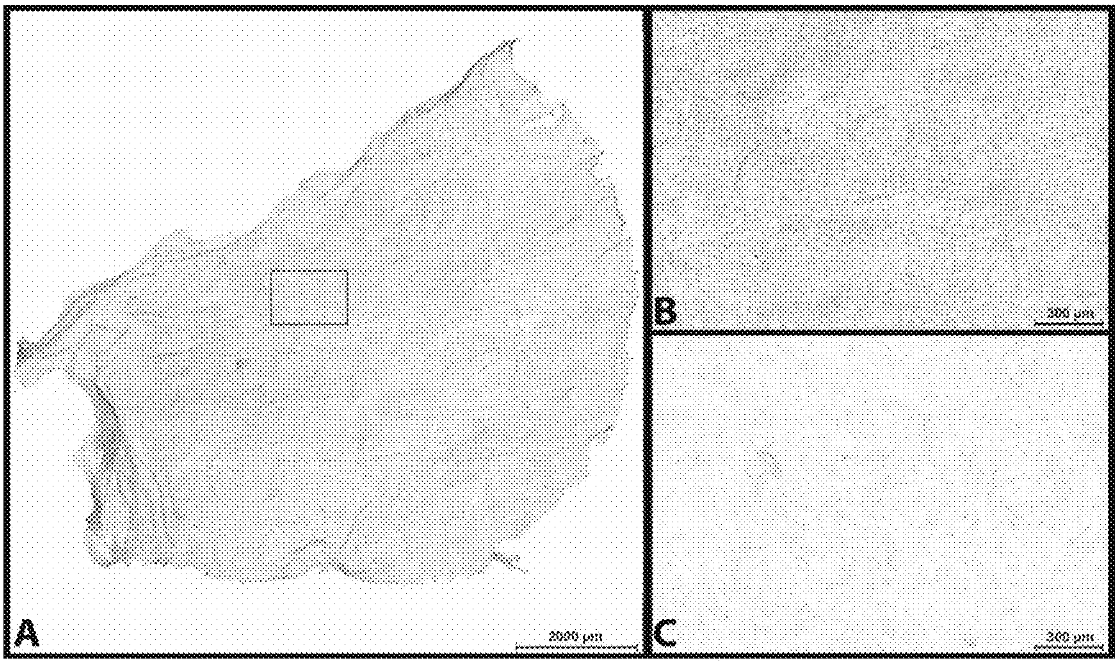
FIG. 3 shows an anti-LAMP-1 staining of keratinocyte cell layer, which is typical, yet exemplary of senescent cells that can be used in an embodiment of the present invention.
Figure 4:
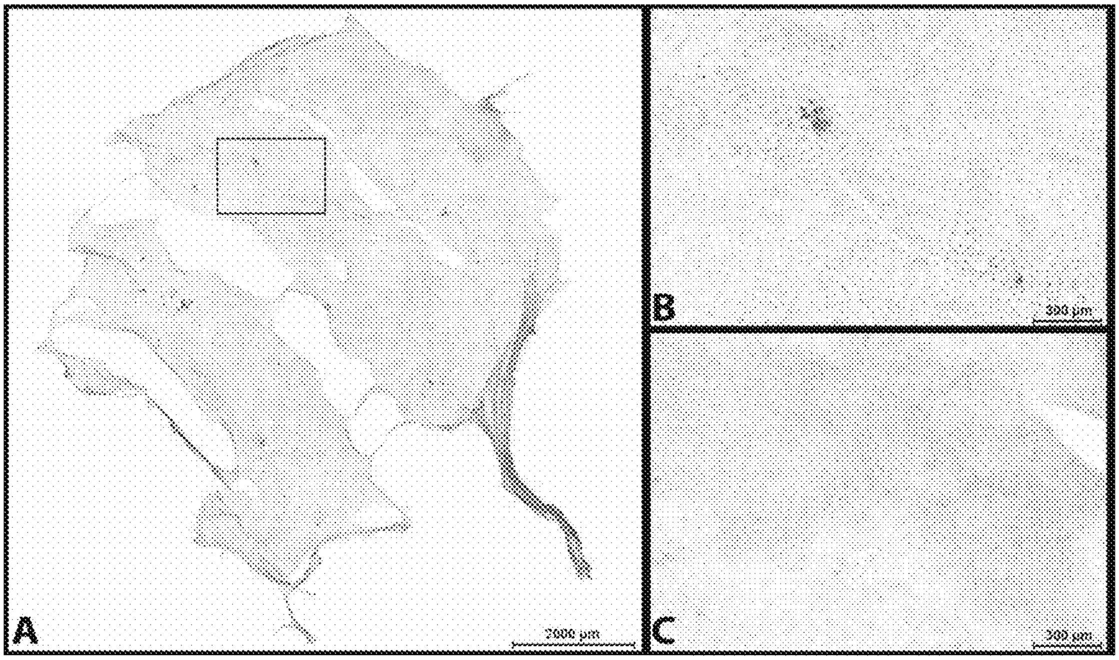
FIG. 4 shows an anti-phospho-histone H2A.X staining of keratinocyte cell layer, which is typical, yet exemplary of senescent cells that can be used in an embodiment of the present invention.

As shown in FIGS. 3 (A and B) sections stained vs. LAMP 1 show a strong ubiquitous dotted stain which is typically for senescent cells but no unspecific staining for the secondary antibody. Sections stained vs. the H2A.X senescence marker show a stronger nuclear staining but no unspecific staining for the secondary antibody FIGS. 4 (A-C).

Example 3

Therapeutic Effect of Senescent Keratinocytes

The wound dressing obtained by a method according to Example 1 and/or 2 improves wound healing as analyzed in a clinical study with patients suffering from grade 2 burns and data are summarized in FIG. 3 below. Briefly, 297 patients with an age between 2 months and 16 years were included into the study which was well gender balanced (45% female/55% male). The main cause of burns were scalds and the median total burned surface area of the patients was around 12%. The treatment resulted in an epithilisation of the wounds occurring in 6 days (median). 52% of the patients showed a healing after 6 days, 78% or 95% of the patients show a healing after 9 or 14 days (FIG. 5).

Example 4

SASP Profile Depending on Growth Stimulus

Human primary keratinocytes (BKB12002) derived from neonatal foreskin (De Corte, Verween et al. 2012) were cultivated on collagen I coated 6 well plates using EpiLife medium+S7 supplement from Gibco™. Components delivering a growth stimulus in the S7 supplement are for example EGF, TGF-β and insulin. Cells were grown to 80% confluence, the medium was removed and the cells were further cultivated for 7 days using EpiLife medium without; with 0.5× or with 1.0× S7 supplement providing the growth stimulus. Supernatants from the cell culture wells at the end of the cultivation were collected and protein concentrations of SASP factors were measured as shown in Figure II. Protein concentrations were quantified using the Bio-Plex® Multiplex Immunoassays or ELISA kits from BIO-RAD. FIG. 6 shows the relative change of concentrations of secreted factors compared to the value without S7 based on the mean values from supernatants of two cell culture wells.

Example 5

SASP Profile of Cells in Replicative Senescence

In order to determine the changes in the profile of SASP factors in primary human BKB12002 cells undergoing replicative senescence, cells were grown up to passage 13, at passage 7 and 13, supernatants from the cell culture flasks were collected and protein concentrations of SASP factors were determined. Protein concentrations were quantified using the Bio-Plex® Multiplex Immunoassays or ELISA kits from BIO-RAD. FIG. 7 shows the relative change of concentrations of secreted factors in supernatants from passage 13 compared to the values at passage 7 as based on the mean values from supernatants of two cell culture wells.

Example 6

SASP Profile of Cells Treated with t-BHP or Ethanol

Figure 8:
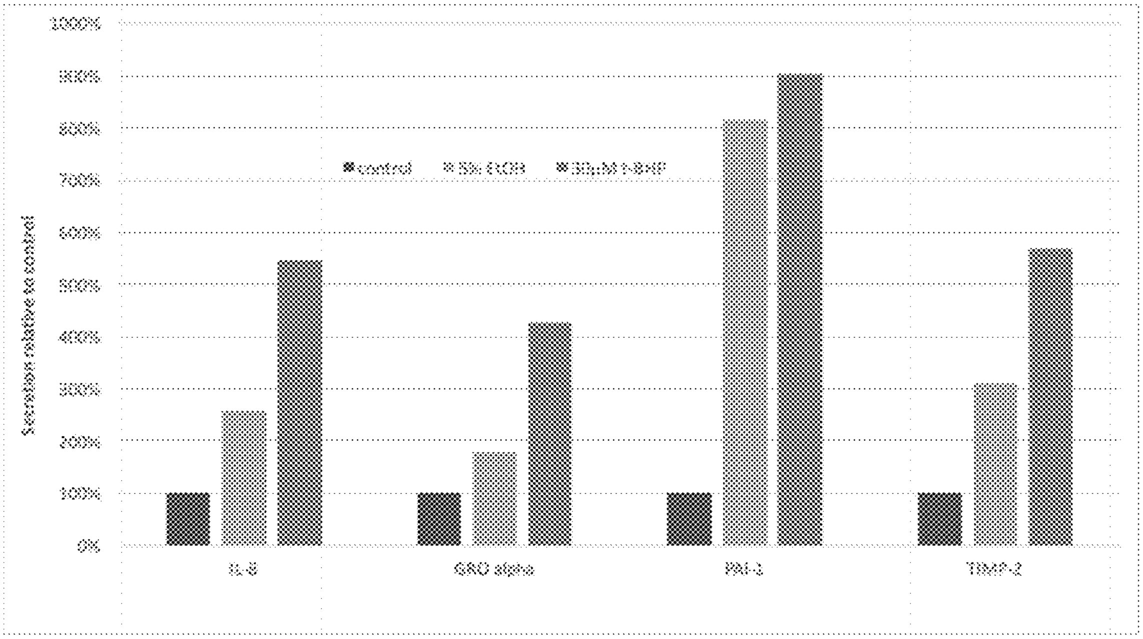
FIG. 8 shows a SASP profile of senescent cells treated with t-BHP or Ethanol.

In order to determine the changes in the profile of SASP factors in cells from a human fibroblasts cell line (SCRC1041) undergoing stress induces senescence, cells were treated with Ethanol or t-BHP as described. Cells were grown to 80% confluence, the medium was removed and the cells were further cultivated for three days with the same medium performing a daily treatment with 5% Ethanol for 2 h or 30 μM t-BHP for 1 h. FIG. 8 summarizes the changes in the levels of secreted SASP factors that were determined as described above.

Example 7

SASP Profile of Cells Treated with Surfactant

Figure 9:
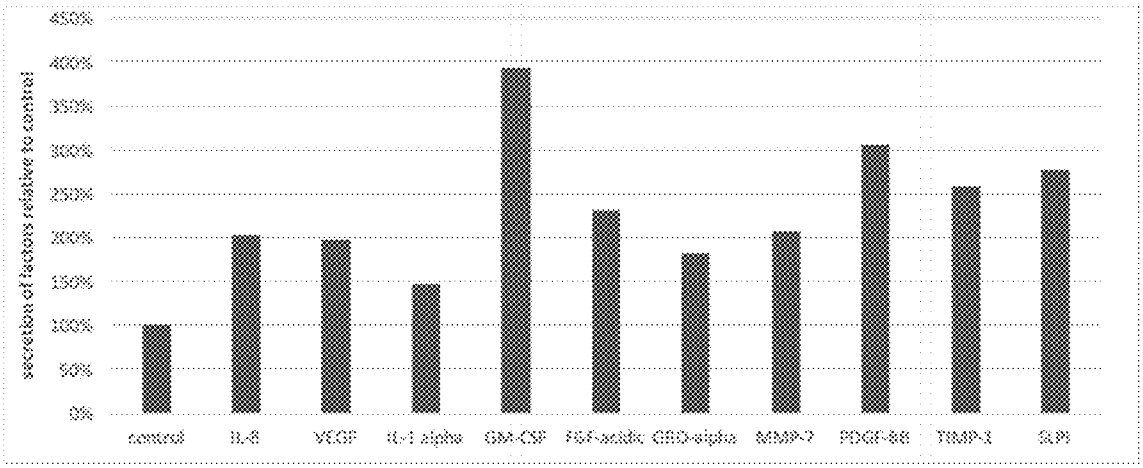
FIG. 9 shows a SASP profile of senescent cells treated with surfactant.

Human primary keratinocyte BKB10002 cells were treated with the surfactant NP40 in order to induce senescence. Cells were grown in EpiLife medium+S7 supplement without (control) or with 2 uM NP40 for 14 days with a medium change every second day. At day 14 of cultivation 11% of the cells showed a positive β-Gal staining using the staining kit from Cell Signaling and the protocol of the manufacturer (not shown). Protein concentrations in the supernatants of the cell cultures were quantified using the Bio-Plex® Multiplex Immunoassays or ELISA kits from BIO-RAD. FIG. 9 shows the relative change of concentrations of secreted factors compared to the control value.

Example 8

Senescence Tests with Irradiated Cells

Figure 10:
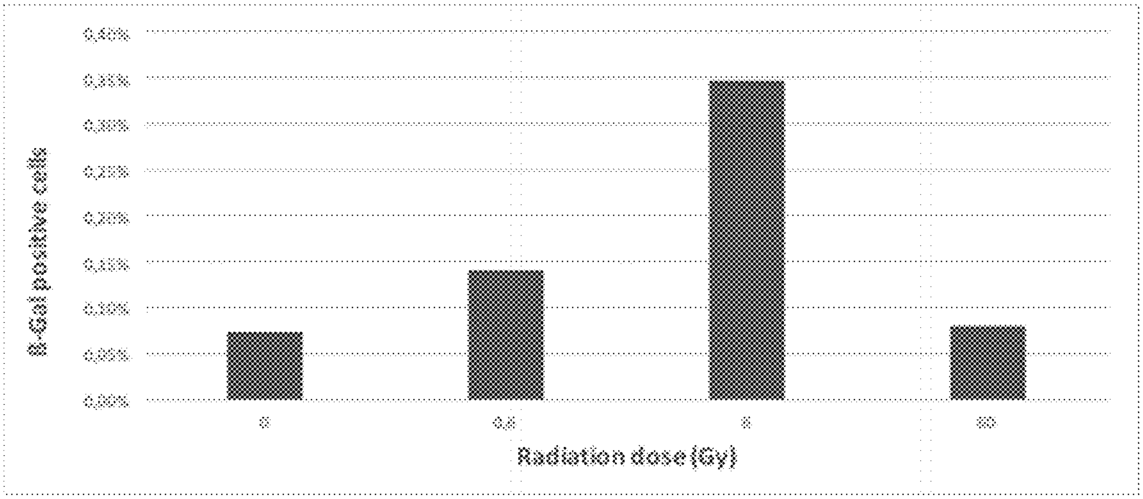
FIG. 10 shows a β-galactosidase staining of irradiated fibroblasts.

In order to determine if human fibroblasts (SCRC1041) treated with different doses of gamma radiation show a senescent phenotype, cells were treated with different doses as shown in FIG. 10. Percentage of β-Gal positive cells were determined as described in example 7.

Example 9

SASP Profile of Cells Treated with Mitomycin

BKB12002 keratinocytes or SCRC1041 fibroblasts were incubated once or repeated times with different doses of mytomycin and the percentage of β-Galactosidase positive cells and the concentration of selected secreted factors was determined.

For the single treatment with mytomycin cells were grown to 80% Cells were grown to 80% confluence using EpiLife medium+S7 supplement from Gibco™ and incubated for 5 h with the same medium including the different concentrations of mytomycin. The medium was removed, cells washed once with PBS and the cells were then further cultivated for 7 days in medium without mytomycin.

For the repeated treatment the BKB12002 cells were cultivated for 2 days using EpiLife medium+S7 supplement from Gibco™ and then for another 12 days with the same medium containing the different amounts of mytomicin and a medium change at every second day. The percentage of senescent cells positive for β-Gal staining was determined using the staining kit Cell Signaling and the protocol of the manufacturer. Protein concentrations in the supernatants of the cell cultures were quantified using the Bio-Plex® Multiplex Immunoassays or ELISA kits from BIO-RAD. FIG. 11 shows the relative fold change of concentrations of secreted factors compared to the control value.

The invention claimed is:

1. A method for treating a tissue for tissue regeneration, comprising providing a composition comprising a cell component, wherein the cell component includes a senescent cell type or a combination of senescent cell types, and applying said composition to the tissue to be treated, wherein the cell component includes mainly one cell type, the cell type being keratinocytes, and wherein at least 85% of all cells in the composition are keratinocytes.

2. The method according to claim 1, wherein the senescent cell type derives from cells selected from the group consisting of epithelial cells, corneal epithelial cells, keratinocytes, fibroblasts, melanocytes, endothelial cells, pericytes, monocytes, lymphocytes, thrombocytes, mast cells, adipocytes, muscle cells, neurons, osteocytes, osteoblasts, chondrocytes, mesenchymal stem cells and/or an adult or embryonic stem cells.

3. The method according to claim 1, wherein the cells are allogeneic, autogeneic or xenogeneic.

4. The method according to claim 3, wherein the cell component includes more than 70% senescent keratinocytes.

5. The method according to claim 3, wherein the cell component includes more than 90% senescent keratinocytes.

6. The method according to claim 5, wherein senescence is induced by cell culture stress, by cell contact inhibition or by administration of surfactants.

7. The method according to claim 1, wherein senescence is characterized by cell cycle arrest in the presence of growth stimulation and/or wherein senescence is induced by cell cycle arrest in the presence of sustained growth stimulation.

8. The method according to claim 1, wherein senescent cells express and/or secrete one or more biologically active molecules selected from the group consisting of: IL-1α, IL-1β, IL-6, IL-7, IL-8, IL-10, IL-13, IL-15, IL-18, MCP1, MCP2, MCP4, MIF, MIP-1a, MIP-3a, HCC-4, Eotaxin-3, TECK, ENA-78, I-309, I-TAC, GROα, GROβ, GROγ, VEGF, EGF, HGF, FGF, bFGF, KGF, Amphiregulin, Angiogenin, APOJ, CAV1, OSTEO, Epiregulin, Heregulin, SCF, SDF-1 alpha, PIGF, IGFBP-2, -3, -4, -6, -7,GM-CSF, PDGF-BB, TGF-α, TGF-β1, TGF-β2, TGF-β3, ICAM1, ICAM3, TRAIL-R3, Fas, OPG, SGP130, EGF-R uPAR, sTNFRI, sTNFRIII, MMP1, MMP2, MMP3, MMP7, MMP9, MMP10, MMP12, MMP13, MMP14, TIMP1, TIMP2, PAI1, PAI2, Park7DJ-1, uPA/Urokinase, SLPI, Syndecan 1, -4, Tenascin C, Endothelin, Collagens, Fibronectins, Laminins.

9. The method according to claim 1, wherein the treatment is for treating an acute or chronic wound and/or an inflammatory condition.

10. The method according to claim 9, wherein the wound is a burn selected from the group consisting of: superficial and/or deep partial thickness burn, second or third degree burn, sun burn, and/or wherein the wound is a chronic wound-healing disorder selected from the group consisting of ulcers, pressure sores, diabetic foot syndrome.

11. The method according to claim 1, wherein the cell component includes more than 10% senescent cells.

12. The method according to claim 1, wherein the cell component includes more than 50% senescent cells.

13. The method according to claim 1, wherein senescence is induced by cell culture stress selected from the group consisting of: cell overgrowth, cell contact inhibition, high cell density, oxidative stress, presence of reactive oxygen species; administration of surfactants or other small molecule inducers of senescence; senescence-inducing administration of mitomycin C or any other chemically-based mitotic inhibitor; or by irradiation with γ-Rays, irradiation with X-Rays, or irradiation with UV light including UVB; or by treatment with cold plasma, radiation or e-beam treatment.

14. The method according to claim 1, wherein the senescent cells express and/or secrete at least one or more of IL-8, GROα, VEGF, endothelin, MMP7, MMP9, MMP10, MMP12, MMP13, TIMP1, TIMP2 and TGF-β1.

15. The method according to claim 1, wherein senescent cells express and/or secrete one or more biologically active molecules selected from the group consisting of: IL-8, GROα, VEGF, endothelin, MMP7, MMP9, MMP10, MMP12, MMP13, TIMP1, TIMP2, TGF-β1 and/or wherein senescent cells are characterized by one or more features selected from the group consisting of: SA β-gal activity, proliferation arrest, $p16^{INK4a}$ expression, DNA-damage signalling, telomere dysfuntion, loss of lamin B1.

* * * * *